US009117166B2

(12) United States Patent
Reynolds, IV et al.

(10) Patent No.: US 9,117,166 B2
(45) Date of Patent: Aug. 25, 2015

(54) MEASUREMENT PROBE WITH HEAT CYCLE EVENT COUNTER

(71) Applicant: BROADLEY-JAMES CORPORATION, Irvine, CA (US)

(72) Inventors: William E. Reynolds, IV, Irvine, CA (US); Robert J. Garrahy, Walnut, CA (US); Andrew W. Hayward, Flitwick (GB); Robert Fish, Rancho Cucamonga, CA (US); Jared H. Nathanson, Mission Viejo, CA (US); Scott T. Broadley, Laguna Beach, CA (US)

(73) Assignee: Broadley-James Corporation, Irvine, CA (US)

( * ) Notice: Subject to any disclaimer, the term of this patent is extended or adjusted under 35 U.S.C. 154(b) by 0 days.

(21) Appl. No.: 14/207,347

(22) Filed: Mar. 12, 2014

(65) Prior Publication Data

US 2014/0301525 A1    Oct. 9, 2014

Related U.S. Application Data

(60) Provisional application No. 61/794,355, filed on Mar. 15, 2013.

(51) Int. Cl.
*G01K 1/02* (2006.01)
*G06M 1/10* (2006.01)
*G01K 13/00* (2006.01)
*A61L 2/00* (2006.01)
*A61L 9/00* (2006.01)

(52) U.S. Cl.
CPC .. *G06M 1/10* (2013.01); *A61L 2/00* (2013.01); *A61L 9/00* (2013.01); *G01K 13/00* (2013.01)

(58) Field of Classification Search
USPC .......................................... 377/15, 19, 25, 26
See application file for complete search history.

(56) References Cited

U.S. PATENT DOCUMENTS 4,195,349 A * 3/1980 Balkanli ......................... 702/98
5,452,335 A * 9/1995 Slater et al. ..................... 377/25
(Continued)

FOREIGN PATENT DOCUMENTS

DE    10 2007 039 088 A1    2/2009

OTHER PUBLICATIONS

International Search Report for International Application No. PCT/US2014/025025, dated Sep. 9, 2014.
(Continued)

*Primary Examiner* — William Hernandez
(74) *Attorney, Agent, or Firm* — Knobbe Martens Olsen & Bear LLP

(57) ABSTRACT

A measurement device is disclosed, embodiments of which are adapted to withstand, detect, and record detection of heat cycle events, including autoclave cycles. Embodiments of the measurement device comprise a sensor for measuring a characteristic of a medium and a heat cycle detection unit. Embodiments of the heat cycle detection unit comprise a temperature or atmospheric pressure responsive element, a detection module, data interface, and data memory. In one disclosed embodiment, the temperature or pressure responsive element is configured to respond to a characteristic of a heat cycle event while the heat cycle detection unit is off. In another disclosed embodiment, the detection module is configured to automatically power off the heat cycle detection unit in response to detecting an autoclave cycle. Methods of using the devices are also disclosed.

20 Claims, 11 Drawing Sheets

(56) References Cited

U.S. PATENT DOCUMENTS

| | | | |
|---|---|---|---|
| 6,166,538 A | 12/2000 | D'Alfonso | |
| 6,295,330 B1 * | 9/2001 | Skog et al. | 377/15 |
| 6,421,193 B1 * | 7/2002 | Li | 360/25 |
| 2008/0130706 A1 * | 6/2008 | Kellner et al. | 374/45 |
| 2009/0251152 A1 * | 10/2009 | Ammann | 324/459 |
| 2011/0034910 A1 | 2/2011 | Ross | |

OTHER PUBLICATIONS

Written Opinion of the International Searching Authority for International Application No. PCT/US2014/025025, dated Sep. 9, 2014.

* cited by examiner

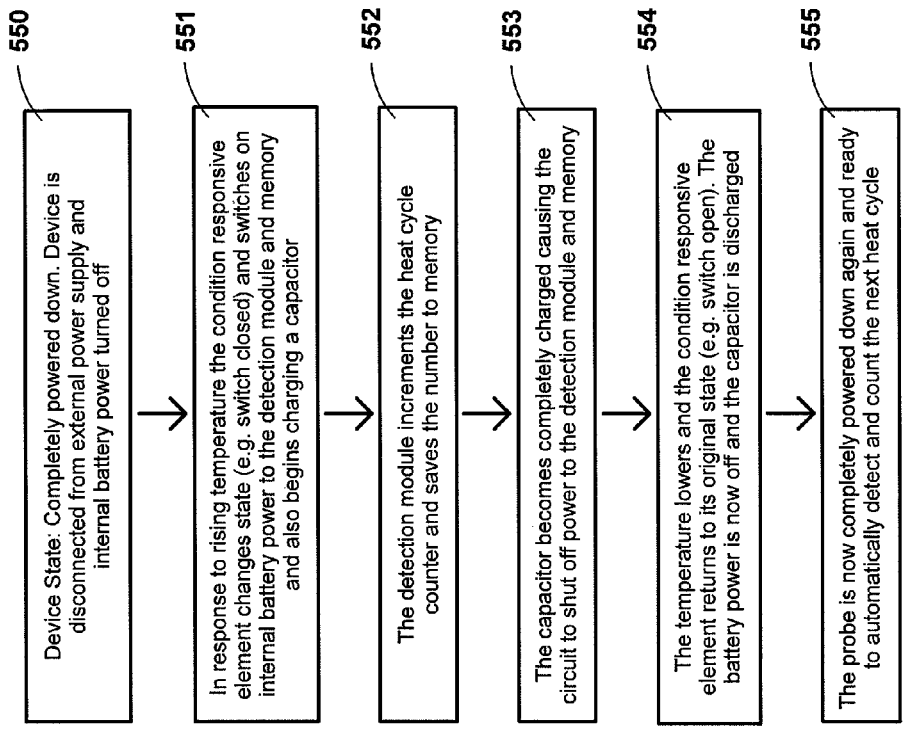
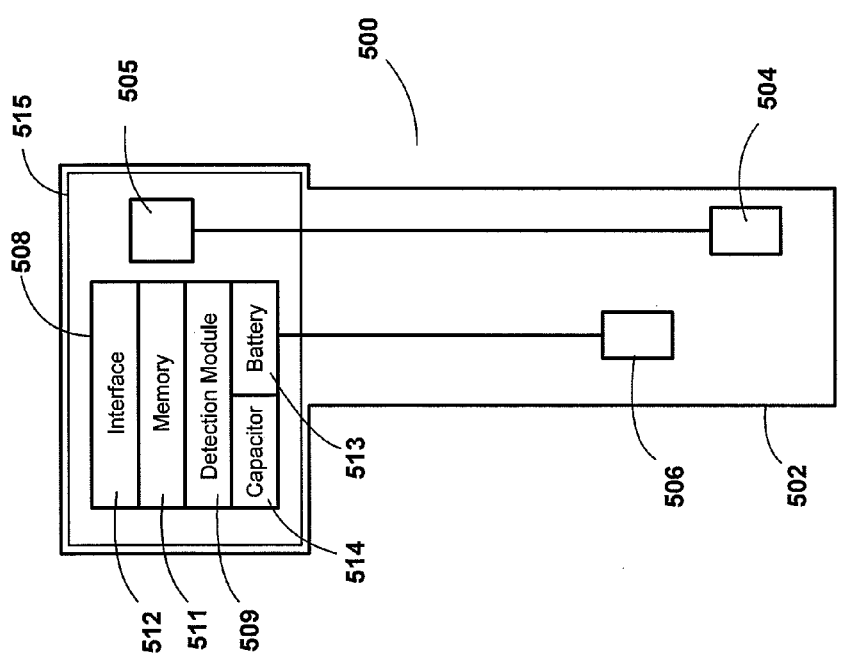
Fig. 5B
Fig. 5A

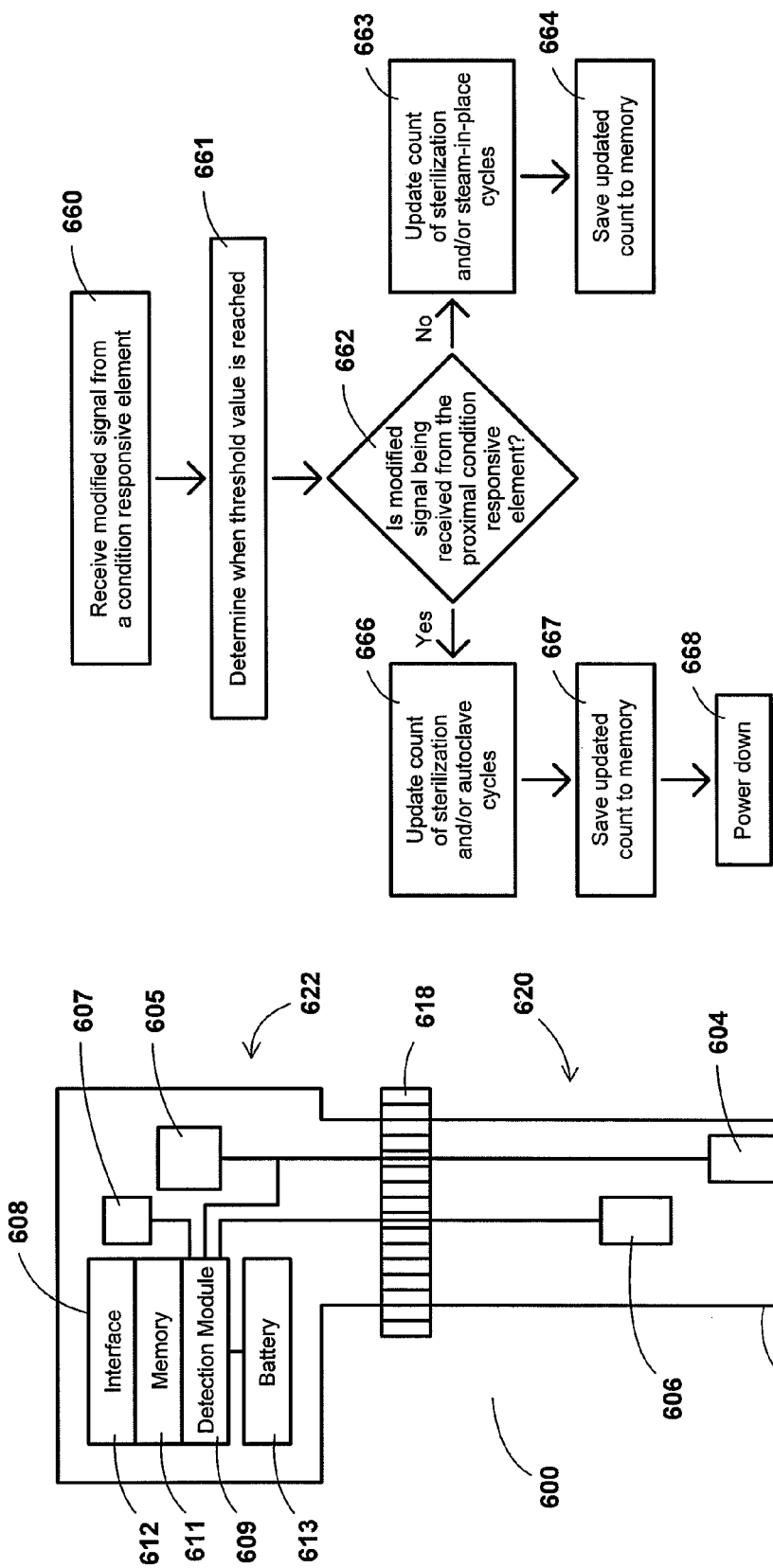

MEASUREMENT PROBE WITH HEAT CYCLE EVENT COUNTER

BACKGROUND

1. Field of the Invention

The present invention relates to measurement probes. More particularly, the invention relates to devices and methods used to detect and count heat cycles experienced by measurement probes.

2. Description of the Related Art

Control of industrial processes is largely dependent on measurement signals received from measurement devices within process mediums. Measurement probes, which are equipped with sensors such as pH sensors, temperature sensors, redox sensors, carbon dioxide sensors, and dissolved oxygen sensors, are frequently used to monitor biological and chemical processes in the fields of biotechnology, pharmaceuticals, and food/beverage processing. In such industries, accuracy of measurements is critical.

In such industries, sterilization or cleaning is also critical. Frequent sterilization or cleaning is often required in these industries, because bacteria and other microorganisms may proliferate on unsterilized surfaces and create health risks. Additionally, sterilization or cleaning of measurement probes is needed to prevent contamination deposits from building up on the surface of the probes where they can introduce errors into the measurement signals.

Three sterilization or cleaning methods are frequently employed to sterilize equipment used in biological or chemical processes: steam-in-place sterilization, clean-in-place, and autoclaving. Steam-in-place sterilization procedures allow for in-line pressurized steam sterilization of all surfaces located within the interior of a reaction vessel or other processing container (herein referred to as a processing vessel), thus providing for sterilization without disassembly. Clean-in-place procedures allow for in-line cleaning by flushing the process vessel and associated piping with sanitizing chemical solutions at elevated temperatures. Autoclaving involves subjecting the processing vessel and the entire probe, to pressurized steam heat within a separate autoclave chamber. Autoclaving is often a preferred method of sterilization at least in part when the processing vessel is relatively small and transportable to the autoclave chamber. The major drawback to autoclaving is that the entire probe body is subjected to the high sterilization temperature and this can have a detrimental effect on any internal circuitry that is powered up at the time. If the probes is externally powered then it must be disconnected from its signal and/or power cable before it is placed in the autoclave. In many industries, subjecting the process vessel, probes, and associated equipment to high pressure steam at 121° C. in an autoclave for 20-30 minutes is sufficient to achieve sterilization. However, it is not uncommon to find that the vessel, probes, and associated equipment are exposed to pressurized steam at temperatures in excess of 130° C. and for periods of 60 minutes or longer to insure complete sterilization.

Measurement probes can experience structural changes, aging, and decreased functionality and accuracy through exposure to extreme conditions. Particularly, the rapid increase and decrease of temperature associated with common steam heat sterilization or hot chemical solution cleaning methods leads to probe degradation; thus, measurement probes are consumable products which must be replaced regularly. In industry, a balance is required when determining how frequently to replace measurement probes. Premature exchange of probes unnecessarily increases costs, whereas a probe that has reached the end of its life may fail during use. Loss of the probe measurement in mid-process often results in loss of process control and the subsequent ruin of an entire biological or chemical batch, leading to costly waste and delays. Accordingly, it is important for the probe operator to monitor the condition and evaluate the fitness for service of industrial measurement probes by tracking the number of heat cycles that it has experienced.

SUMMARY

The present disclosure describes devices and methods used to detect and count heat cycles experienced by measurement probes, particularly heat cycles associated with steam heat sterilization and hot chemical solution cleaning procedures. These procedures are among the greatest contributors to probe degradation and failure. Accordingly, by providing means for detecting and maintaining a count of the heat cycles associated with these procedures, the devices and methods described herein will help probe operators determine the risk associated with continued use of the probe and determine when it is time to replace the measurement probes.

The embodiments disclosed herein each have several innovative aspects, no single one of which is solely responsible for the desirable attributes of the invention. Without limiting the scope, as expressed by the claims that follow, the more prominent features will be briefly disclosed here. After considering this discussion, one will understand how the features of the various embodiments provide several advantages over current measurement probes.

One aspect of the disclosure is a measurement device adapted to withstand and automatically detect a heat sterilization or cleaning cycle and increment and maintain a counter of the total number of cycles for later review by the operator, particularly when the measurement device is disconnected from all external power sources. The device includes a measurement probe including a sensor configured to detect a characteristic of a medium and generate a measurement signal; a condition responsive element including either a temperature responsive element or an atmospheric pressure responsive element; and a heat cycle detection unit including a detection module, a data interface, and a data memory. The detection module is configured to detect a heat cycle event using the condition responsive element, and record detection of the heat cycle event in the data memory. In some embodiments the heat cycle event is part of an autoclave procedure, a steam-in-place sterilization procedure, or a clean-in-place procedure. In some embodiments the device is configured to automatically power up the heat cycle detection unit as soon as the heat cycle is detected, the heat cycle detection unit then increments a counter, and then the device powers itself off to protect the circuit from prolonged and excessive heat exposure as in the case of an autoclave procedure where the entire probe is autoclaved. In some other embodiments the device will automatically turn itself back on when the heat cycle is complete and the device has cooled off to a safe operating temperature. In some embodiments, the device will automatically turn itself back on when the heat cycle is complete and the device has cooled off to a safe operating temperature, at which point the device records the occurrence of the heat cycle, and then the device automatically powers off until the next heat cycle is detected. In other embodiments the device will remain off to conserve battery power and only turn itself back on briefly when another heat cycle is detected and the cycle needs to be counted by the heat cycle detection unit. In some embodiments, the measurement probe and the heat cycle detection unit are separably connected. In other embodiments, the measurement probe and the heat cycle detection unit are fixedly integrated.

In some embodiments, the condition responsive element is a first switch configured to transition from a first state to a second state when the first switch exceeds a first temperature or a first pressure. In such embodiments, the detection module is configured to record detection of a heat cycle event in the data memory in response to the first switch transitioning from the first state to the second state. The measurement device may further include a capacitor coupled to the first switch, which is configured to discharge in response to the first switch transitioning from the first state to the second state. In such embodiments, the detection module need not be powered up during an autoclave cycle but is configured to detect the discharged capacitor and record detection of a heat cycle event in the data memory after the autoclave detection unit is powered back on following an autoclave cycle. The first switch changes to its second state at some pre-defined temperature that marks the beginning of the heat cycle. This second state discharges a capacitor. When the detection module powers back up it detects the discharged capacitor and increments the event counter.

In some embodiments, the measurement device also includes a portable power source in addition to, or instead of, a capacitor. In such embodiments, the detection module is configured to record detection of a heat cycle event in the data memory in response to a temperature responsive element exceeding a first temperature or an atmospheric pressure responsive element exceeding a first pressure. After the counter is incremented the autoclave detection unit is configured to power off in response to the temperature responsive element exceeding the first temperature or in response to the atmospheric pressure responsive element exceeding the first pressure. In some such embodiments, the measurement device includes a second switch configured to transition from a power-off state to a power-on state when the second switch falls below a power-on temperature or a power-on pressure. In such embodiments, the autoclave detection unit is configured to automatically power on when the second switch transitions from the power-off state to the power-on state. In some embodiments, the second switch and the condition responsive element are one and the same; a universal switch can acts as both the second switch and the condition responsive element.

The first switch and/or the second switch in various embodiments are selected from the group consisting of: a bimetallic strip, an integrated thermal switch, and a pressure switch. The condition responsive element of other embodiments may be selected from the group consisting of: a resistance temperature detector, a bimetallic strip, an integrated thermal switch, a positive temperature coefficient thermistor, switching PCT thermistor, or other thermistor, a pressure switch, a piezoelectric pressure sensor, an electromagnetic pressure sensor, a capacitive pressure sensor, and a piezoresistive strain gauge. In various embodiments, the first temperature and/or power-on temperature are within a range of 50 to 120 degrees Celsius, and the first pressure and/or power-on pressure are within a range of 15 to 45 psi.

In some embodiments, the measurement device also includes a coupling element configured to engage with a vessel body such that, when the coupling element is engaged with the vessel body, the measurement device includes a distal portion that is positioned within a vessel cavity and a proximal portion that is positioned external to the vessel cavity. In some such embodiments, the condition responsive element is positioned in or on the distal portion. In other embodiments, the condition responsive element is positioned in or on the proximal portion. When the condition responsive element is positioned in or on the proximal portion, the measurement device may additionally include a vessel temperature responsive element positioned in or on the distal portion. In such embodiments, the detection module is configured to detect a heat cycle event and record detection of the heat cycle event in the data memory in response to either the condition responsive element exceeding a first temperature or pressure or the vessel temperature responsive element exceeding a vessel sterilization temperature. Additionally, in such embodiments, the detection module may be configured to detect an autoclave cycle and record detection of the autoclave cycle in the data memory in response to the condition responsive element exceeding a first temperature or pressure, and the module may be further configured to detect a steam-in-place cycle and record detection of the steam-in-place cycle in the data memory in response to only the vessel temperature responsive element exceeding the vessel sterilization temperature. The autoclave detection unit can be configured to power off when an autoclave cycle is detected and optionally power off when a steam-in-place cycle is detected.

In some embodiments both a condition responsive element and a temperature responsive element are located in the distal end of the measurement device and another temperature responsive element is located in the proximal end of the device. When a preset temperature limit is exceeded in the sterilization or cleaning procedure in the distal end of the device, the condition responsive element changes state and powers on the circuit in the detector module. The module then increments the heat cycle counter and additionally uses the temperature responsive element in the distal end to measure additional information such as maximum heat exposure and length of exposure time in the case of steam-in-place or clean-in-place procedures. The temperature responsive element in the proximal end is also powered on and it monitors the device temperature at the proximal end. If the proximal temperature exceeds a preset limit then the device logic determines that the device is being autoclaved and the circuit completely shuts down after incrementing the heat cycle counter.

In some embodiments, the measurement device also includes a pH sensor positioned in the distal portion. In one such embodiment, a condition responsive element in the distal end can change state due to a process heat cycle and switch on the device's power and the detection module can be configured to differentiate and detect a clean-in-place cycle and record detection of the clean-in-place cycle when a distally-located temperature responsive element exceeds a clean-in-place temperature and a measurement from the pH sensor exceeds a clean-in-place pH level, both within a defined period of time. The distally-located temperature responsive element of some embodiments is the vessel temperature responsive element disclosed above. In at least some embodiments, the clean-in-place temperature is within a range of 65 to 95 degrees Celsius, and the clean-in-place pH is within the extreme ranges of either 9 to 14 pH or 1 to 4 pH.

In various embodiments, the first temperature and/or the vessel temperature are within a range of 50 to 120 degrees Celsius, and the first pressure is within a range of 15 to 45 psi. The measurement probe is selected from the group consisting of an amperometric, a potentiometric, an optical, a capacitive, and a conductive probe. Additionally, in some embodiments, the sensor is selected from the group consisting of a pH sensor, a temperature sensor, a dissolved oxygen sensor, and a combination thereof. The detection module of some embodiments is selected from the group consisting of a circuit, a microprocessor, a Digital Signal Processor, an Application Specific Integrated Circuit, and a Field Programmable Gate Array. The data interface of some embodiments is selected from the group consisting of a wireless transmitter, an input/output terminal, a data bus, a contactless inductive coupling interface (see e.g. DE 19540854A1, DE 4344071A1, and U.S. Pat. Nos. 7,785,151, 6,705,898, 6,476, 520; each of which is incorporated herein by reference in its entirety and for disclosure thereof), and an industry standard 8 pin connector. In some embodiments, the measurement device also includes a power-gathering system, such as, for example, a photodiode or a photovoltaic cell.

An additional aspect of the disclosure is a method of automatically counting autoclave and other heat sterilization cycles and/or cleaning cycles experienced by any embodiment of the measurement device described above, while protecting the circuitry contained within the measurement device and managing the device's power supply. The method includes detecting a heat sterilization cycle using a first temperature responsive element that is configured to respond when the temperature exceeds a first temperature, automatically powering up the detection unit circuitry if off, recording detection of the heat sterilization cycle in a data memory and incrementing a counter, and automatically powering off the detection unit circuitry after detection of the heat sterilization cycle, if it is desired in a particular process procedure to protect the device's circuit from excessive heat during the heat cycle and to conserve the device's power.

Another aspect of the disclosure is a method of automatically counting a heat cycle experienced by a measurement device. The method includes providing a measurement device, the device including a measurement probe having a sensor configured to detect a characteristic of a medium and generate a measurement signal, a condition responsive element, and a heat cycle detection unit having a detection module, a data interface, and a data memory. The method further includes detecting a heat cycle event, using the condition responsive element and recording detection of the heat cycle event in the data memory. In some embodiments, the heat cycle event is an autoclave cycle, a steam-in-place sterilization event, or a clean-in-place event. In some embodiments, the device is configured to automatically power up the heat cycle detection unit after detection of the heat cycle event and then, after incrementing the counter, power it down if the heat cycle event comprises an autoclave cycle.

In some embodiments of the method, the condition responsive element is a first switch that transitions from a first state to a second state when the first switch exceeds a first temperature or a first pressure, and the detection module records detection of a heat cycle event in the data memory in response to the first switch transitioning from the first state to the second state. In some such embodiments, the method also includes discharging a capacitor coupled to the first switch in response to the first switch transitioning from the first state to the second state. In such embodiments, detecting a heat cycle event using the condition responsive element involves detecting a discharged capacitor. In some such embodiments, detecting a discharged capacitor and recording detection of a heat cycle event in the data memory occur after the autoclave detection unit is powered on following an autoclave cycle.

In some embodiments of the method, the autoclave detection unit receives power from a portable power source electrically coupled to the measurement device. The detection module of some such embodiments records detection of a heat cycle event in the data memory in response to the condition responsive element exceeding a first temperature or a first pressure. The autoclave detection unit of some such embodiments powers off in response to the condition responsive element exceeding the first temperature or the first pressure. In some embodiments, the method additionally includes automatically powering on the autoclave detection unit when a second switch in the measurement device transitions from a power-off state to a power-on state. In such embodiments, the second switch transitions from the power-off state to the power-on state when the second switch falls below a power-on temperature or pressure. In some embodiments, a universal switch within the measurement device includes both the second switch and the condition responsive element.

In various embodiments of the method, the first temperature and/or the power-on temperature are within a range of 50 to 120 degrees Celsius, and the first pressure and/or the power-on pressure are within a range of 15 to 45 psi.

The method of some embodiments also includes engaging with a vessel body such that a distal portion of the measurement device is positioned within a vessel cavity and a proximal portion of the measurement device is positioned external to the vessel cavity. In some such embodiments, the condition responsive element is positioned in or on the distal portion. In other embodiments, the condition responsive element is positioned in or on the proximal portion.

In some embodiments having the condition responsive element positioned in or on the proximal portion, the detection module detects a heat cycle event and records detection of the heat cycle event in the data memory in response to either the condition responsive element exceeding a first temperature or first pressure or a vessel temperature responsive element positioned in or on the distal portion exceeding a vessel sterilization temperature. In some such embodiments, the step of detecting a heat cycle event and recording detection of the heat cycle event in the data memory includes one of: detecting an autoclave cycle and recording detection of the autoclave cycle in the data memory in response to the condition responsive element exceeding a first temperature or a first pressure, or detecting a steam-in-place cycle and recording detection of the steam-in-place cycle in the data memory in response to the vessel temperature responsive element exceeding the vessel sterilization temperature and the condition responsive element not exceeding a first temperature or a first pressure. In some such embodiments, the autoclave detection unit powers off when an autoclave cycle is detected and optionally powers off when a steam-in-place cycle is detected.

In the method of some embodiments, the detection module detects a clean-in-place cycle and records detection of the clean-in-place cycle when: (1) a temperature responsive element located in or on the distal portion exceeds a clean-in-place temperature, and (2) a measurement from a pH sensor positioned in the distal portion exceeds a clean-in-place pH level, both within a defined period of time. In some such embodiments, the temperature responsive element located in or on the distal portion is the vessel temperature responsive element.

In some embodiments of the method, the clean-in-place temperature is within a range of 65 to 90 degrees Celsius and/or the clean-in-place pH is within a range of either 9 to 14 pH or 1 to 4 pH. Additionally or alternatively, in some embodiments, the first temperature and the vessel temperature are within a range of 50 to 120 degrees Celsius and the first pressure is within a range of 15 to 45 psi.

BRIEF DESCRIPTION OF THE DRAWINGS

The above-mentioned aspects, as well as other features, aspects, and advantages of the present technology will now be described in connection with various embodiments, with reference to the accompanying drawings. The illustrated embodiments, however, are merely examples and are not intended to be limiting. Throughout the drawings, similar symbols typically identify similar components, unless context dictates otherwise. Note that the relative dimensions of the following figures may not be drawn to scale.

FIG. 5A depicts a block diagram of another embodiment of a measurement device.

FIG. 5B is a flowchart illustrating one method of operations performed by the measurement device of FIG. 4A.

FIG. 6A depicts a block diagram of another embodiment of a measurement device.

FIG. 6B is a flowchart illustrating one method of operations performed by the measurement device of FIG. 5A.

DETAILED DESCRIPTION OF VARIOUS EMBODIMENTS

Figure 1:
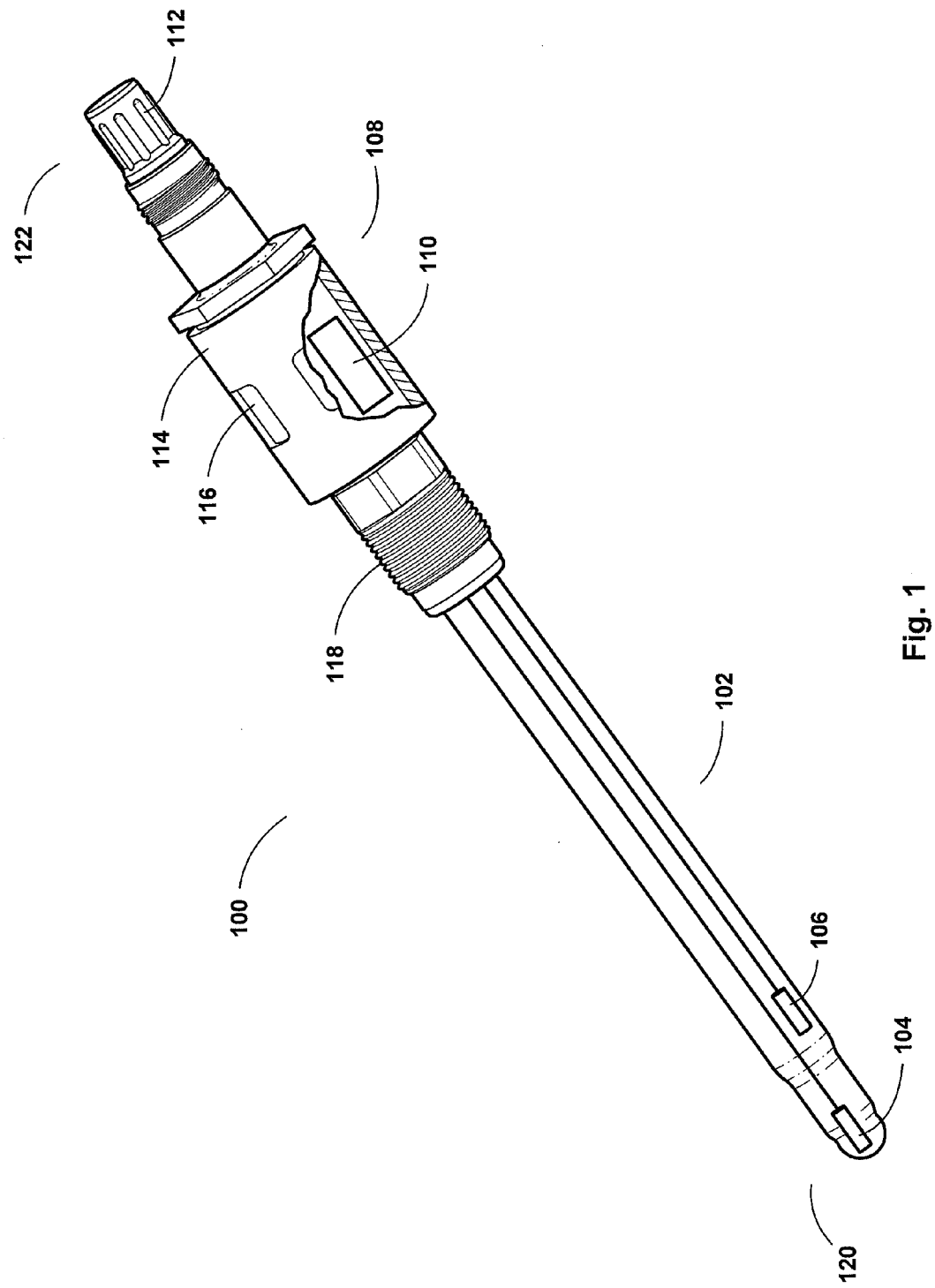
FIG. 1 depicts a perspective view of one embodiment of a measurement device.

In the following detailed description, reference is made to the accompanying drawings, which form a part of the present disclosure. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and form part of this disclosure.

The terminology used herein is for the purpose of describing particular embodiments only and is not intended to be limiting of the disclosure. It will be understood by those within the art that if a specific number of a claim element is intended, such intent will be explicitly recited in the claim, and in the absence of such recitation, no such intent is present. For example, as used herein, the singular forms "a", "an" and "the" are intended to include the plural forms as well, unless the context clearly indicates otherwise. As used herein, the term "and/or" includes any and all combinations of one or more of the associated listed items. It will be further understood that the terms "comprises," "comprising," "includes," and "including," when used in this specification, specify the presence of stated features, integers, steps, operations, elements, and/or components, but do not preclude the presence or addition of one or more other features, integers, steps, operations, elements, components, and/or groups thereof. Expressions such as "at least one of," when preceding a list of elements, modify the entire list of elements and do not modify the individual elements of the list.

To assist in the description of the devices and methods described herein, some relational and directional terms are used. "Connected" and "coupled," and variations thereof, as used herein include direct connections, such as being contiguously formed with or attached directly to, on, within, etc. another element, as well as indirect connections where one or more elements are disposed between the connected elements. "Connected" and "coupled" may refer to a permanent or non-permanent (i.e., removable) connection.

"Secured" and variations thereof as used herein include methods by which an element is directly fastened to another element, such as being glued, screwed or otherwise affixed directly to, on, within, etc. another element, as well as indirect means of attaching two elements together where one or more elements are disposed between the secured elements.

"Proximal" and "distal" are relational terms used herein to describe position. For clarity purposes only, in this disclosure, position is viewed from the perspective of an individual operating a measurement device positioned partially within a processing vessel. The portion of the measurement device located external to the vessel is viewed as being closest, and therefore, most proximal to the operator. The portion of the device positioned within the container is more distally located.

There is a need for a measurement probe that monitors and quantifies its own usage and operational fitness in the bioprocess industries. A leading cause of probe degradation in bioprocess applications is the thermo shock associated with the increase and decrease of temperature associated with some heat sterilization procedures that utilize pressurized steam and cleaning procedures that utilize hot sanitizing chemical solutions. A bioprocess industry standard for keeping track of wear on a measurement probe is the number of these heat cycles experienced by the probe. In some applications, probes are exposed to no more than two to ten heat cycles before being retired. In other applications, the count may be higher. The particular number of heat sterilization or cleaning cycles that a probe can withstand varies by probe manufacturer, sterilization or cleaning method, operator maintenance, and the environmental conditions within the processing medium; thus, probe operators familiar with their unique uses and processes are best equipped to predict the lifespans of their respective probes. Currently, however, in bioprocess laboratory and production settings, it is often easy to lose track of the number of heat sterilization or cleaning cycles experienced by each probe.

Accordingly, there is more than one probe design currently on the market that is configured to detect and record steam-in-place sterilization cycles. However, the design of such probes renders them inoperable during autoclave cycles. In the current models, the probes must be unplugged and fully powered down before being placed in an autoclave chamber; as a result, they can neither detect nor count autoclave cycles. Without being able to automatically detect and count this widely used sterilization method, in many bioprocess applications the current generation of sterilization-counting probes provides little benefit over conventional probe designs. In addition, probes are often disconnected from external power sources during steam-in-place cycles to avoid damaging cables which may come in contact with steam supply pipes or the hot vessel wall. Probes which require an external power source to detect and record steam-in-place cycles will not record the steam-in-place event if the operator disconnects the probe cables.

Another existing probe design uses recorded temperature and time-at-temperature data to self-calculate the length of its remaining lifespan. However, these calculations can provide probe lifespan estimates that are not particularly accurate for the application at hand. This can lead the process operator into a false sense of safety as he reuses a probe that self-predicts that it has plenty of lifespan left and then the probe fails. Lifespans vary across industries and companies and are dependent on nearly innumerable factors. Additionally, the cost of probe failure, and thus, the willingness to accept risk of probe failure, varies across companies.

Various embodiments disclosed herein may overcome some or all of the deficiencies mentioned above. The embodiments relate to devices and methods used to monitor and quantify the usage and operational fitness of measurement probes by automatically (without user input) counting heat cycle events experienced by said probes, even when disconnected from external power supplies. The measurement devices of various embodiments are each configured to detect exposure to heat sterilization or hot chemical cleaning cycles, including autoclave cycles, steam-in-place cycles and/or clean-in-place cycles, and subsequently maintain an accurate count of the sterilization or cleaning cycles experienced. With such an accurate count, laboratory technicians and other probe operators may be able to easily and efficiently determine when it is time to order new probes and/or throw away existing probes based on their own unique experience with that particular bioprocess application. There is currently no commercial probe in the bioprocess industries that can automatically count and record to memory the number of autoclave cycles that it has experienced. The preferred embodiments disclosed herein provide an accurate count of the heat cycles completely automatically and with no operator input or assistance. It is completely automated. These preferred devices also improve the accuracy of the heat cycle count for probes undergoing steam-in-place and clean-in-place procedures. These devices enable accurate heat cycles counts for probes even when not connected to associated instrumentation for any heat cycle procedure.

As shown in FIG. 1, the measurement device 100 of various embodiments includes at least a measurement probe 102, a condition responsive element 106, and an heat cycle detection unit 108. The measurement probe 102 includes a sensor 104 configured to detect a characteristic of a medium and generate an electrical measurement signal, typically an analog signal. The sensor 104 can be any electrochemical sensor known to those skilled in the art. For example, in some embodiments, the sensor 104 is a pH sensor, a temperature sensor, a dissolved oxygen sensor, or a combination thereof. The measurement probe 102 can be amperometric, potentiometric, optical, capacitive, conductive, or any other suitable probe type known to those skilled in the art.

In various embodiments, the condition responsive element 106 is in the form of a temperature responsive element or an atmospheric pressure responsive element. In the simplest embodiments, the condition responsive element 106 is a mechanical switch or other element that undergoes a physical transformation in response to an environmental trigger. For example, in some embodiments, the condition responsive element 106 is a bimetallic strip (also referred to as a thermostat or thermal switch) or a shape memory alloy, such as, for example, nickel-titanium (Nitinol), which undergoes a physical change in shape when the temperature rises above a certain threshold. In some embodiments, the materials are selected and configured such that the physical change occurs within a temperature range of 50 to 120 degrees Celsius, and more preferably, within a range of 100 to 115 degrees Celsius and any sub-range or value therebetween. For example, the physical transformation may occur at 50° C., 55° C., 60° C., 65° C., 70° C., 75° C., 80° C., 85° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., or 120° C.

In other embodiments, the condition responsive element 106 is an integrated thermal switch or pressure switch, which opens or closes an electrical contact when a threshold temperature or pressure, respectively, has been reached. The threshold temperature may be within the range disclosed above. The threshold pressure may be within a range of 10 to 60 psi, and preferably, within a range of 15 to 45 psi. The threshold pressure may include any sub-range or value therebetween, including, for example, 15 psi, 16 psi, 17 psi, 18 psi, 19 psi, 20 psi, 21 psi, 22 psi, 23 psi, 24 psi, 25 psi, 26 psi, 27 psi, 28 psi, 29 psi, 30 psi, 31 psi, 32 psi, 33 psi, 34 psi, 35 psi, 36 psi, 37 psi, 38 psi, 39 psi, 40 psi, 41 psi, 42 psi, 43 psi, 44 psi, or 45 psi.

In still other embodiments, the condition responsive element 106 is an electrical element, such as a resistive element, which produces a change in the electrical signal at least when a threshold value is reached. In some such embodiments, the threshold value may be any of the threshold temperatures and pressures disclosed above. The condition responsive element 106 of some embodiments is, for example, a positive temperature coefficient thermistor, switching PCT thermistor, or other thermistor, a resistance temperature detector (RTD), a piezoelectric pressure sensor, an electromagnetic pressure sensor, a capacitive pressure sensor, a piezoresistive strain gauge, or any other suitable electrical component known to those skilled in the art.

The heat cycle detection unit 108 preferably includes at least a detection module, a data memory, and a data interface 112. In FIG. 1, the detection module and data memory are not individually visible; however, they are preferably printed on stacked circuit cards 110. The detection module of some embodiments is a general purpose processor. In other embodiments, it is a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any processor, controller, microcontroller, or state machine. A detection module may also be implemented as a combination of computing devices.

The data memory may include Random Access Memory (RAM), flash memory, Read Only Memory (ROM), Electrically Programmable ROM (EPROM), Electrically Erasable Programmable ROM (EEPROM), registers, hard disk, a micro-secure digital (SD) card or other removable disk, or any other suitable form of storage medium known in the art. The data memory is coupled to the detection module such that the module can read information from, and write information to, the data memory. In some but not all embodiments, the data memory is integral to the detection module. The detection module and the data memory of some embodiments reside in an ASIC. In alternative embodiments, the detection module and the data memory reside as individual discrete components.

Continuing with FIG. 1, the data interface 112 allows for the communication of signals and information from the detection module to a data output. In some embodiments, the detection module conditions and/or transforms electrical signals before they reach the data interface 112. Consequently, the data interface 112 of various embodiments transmits analog and/or digital signals. The data interface 112 of some embodiments includes one or more radio frequency transmitters, other wireless transmitters, couplers, universal serial buses (USB) and/or other data buses. In FIG. 1, the data interface 112 comprises an eight-pin connector configured to physically and electrically couple to an external transmitter and power supply (not shown). In some embodiments, the measurement device 100 includes an output component, such as, for example, a display screen or signal lights, to display processed data to a user. In other embodiments, the measurement device 100 transmits the data to an external display screen or other output device via near-field communications, radio frequency signals, Bluetooth signals, or other wireless signals, or through a physical electrical connection (e.g., electrical wires, cables, or connector pins) or a contactless inductive coupling interface (see e.g. DE 19540854A1, DE 4344071A1, and U.S. Pat. Nos. 7,785,151, 6,705,898, 6,476,520; each of which is incorporated herein by reference in its entirety and for disclosure thereof). The data output of various embodiments includes, preferably, a count of autoclave cycles and/or total sterilization or cleaning cycles experienced by the device as well as probe serial ID number, manufactured date, and other meta data useful to the operator.

In some embodiments, the heat cycle detection unit 108 additionally includes a protective housing 114 or other casing that wholly or partially surrounds at least some of the electronic components of the measurement device 100. The housing 114 of FIG. 1 is configured to withstand high temperatures, such as, for example, at least temperatures up to 140 degrees Celsius, and/or from steam and moisture. The housing 114 may be further configured to protect the electronic components disposed within the housing from such temperatures and/or moisture. In the embodiment of FIG. 1, the housing 114 encases stacked circuit cards 110 on which the detection module and the data memory are printed. Additionally, in FIG. 1, the housing 114 includes a plurality of glass or plastic-covered windows 116. The windows are designed to permit the entrance of light into the interior of the housing. In such embodiments, one or more photodiodes or photovoltaic cells (not visible in FIG. 1) are included in the heat cycle detection unit 108 to convert light energy into current or voltage. As described in more detail below, the photodiodes and photovoltaic cells are coupled to batteries and/or capacitors within the system to help replace leaking current or charge. In some embodiments, the windows 116 are covered by a clear plastic or other suitable transparent material. Other embodiments include no windows or only one transparent window.

In some embodiments, such as the embodiment depicted in FIG. 1, the measurement probe 102 and the heat cycle detection unit 108 are fixedly connected. In other embodiments, the measurement probe 102 and the heat cycle detection unit 108 are separably coupled. In some such embodiments, the heat cycle detection unit forms, or is positioned within, a removable cap. In other embodiments, the heat cycle detection unit is positioned within a separate transmitter or dongle.

The measurement device 100 of FIG. 1 further includes a vessel-coupling element 118. The vessel-coupling element 118 is configured to interact with, and securely connect to, a receiving port in a processing vessel (not shown). Such receiving ports may be positioned on the side or in the lid of a processing vessel or in a pipe or channel that is fluidly connected to the processing vessel. In FIG. 1, the measurement device 100 couples to processing vessels via complementary threading. In other embodiments, a snap fit or other suitable connection means is used. Once connected, a distal portion 120 of the measurement device 100, comprising at least the sensor 104, is positioned within an interior of the processing vessel. A proximal portion 122 of the measurement device 100, comprising at least the data interface 112, is positioned outside the processing vessel.

Many of the steps of a method or algorithm and functions described in connection with the embodiments disclosed herein may be embodied directly in hardware, in a software module executed by a processor, or in a combination of the two. All such embodiments are contemplated and incorporated into use of the term: detection module. If implemented in software, the functions may be stored on, or transmitted over as, one or more instructions or code on a tangible, non-transitory computer-readable medium.

The steps the detection module is configured and/or programmed to perform include: detecting a sterilization or cleaning event using the condition responsive element, recording detection of the sterilization or cleaning event in the data memory, and automatically powering off the heat cycle detection unit if the heat cycle detection unit is still on and the detected sterilization or cleaning event includes an autoclave cycle. The logic and processes needed to perform these functions are described in more detail below.

Figure 2:
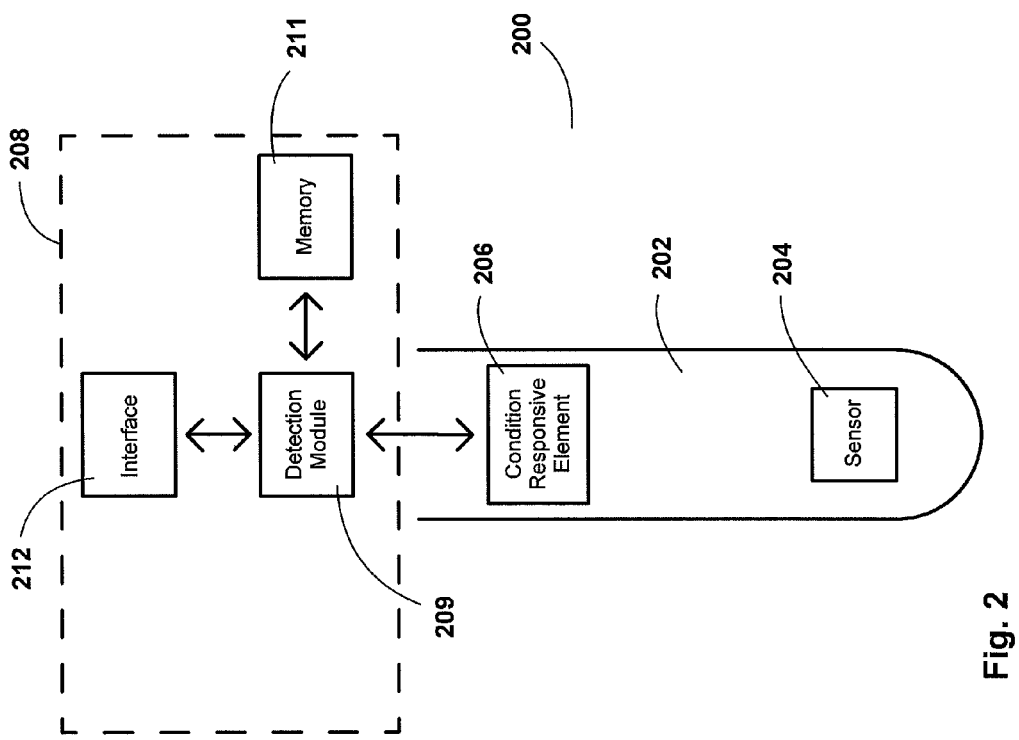
FIG. 2 depicts a block diagram of one embodiment of a measurement device.

In a basic embodiment, such as the embodiment depicted schematically in FIG. 2, the measurement device 200 includes a sensor 204 and a condition responsive element 206 positioned within, or coupled to, a measurement probe 202. The device also includes a heat cycle detection unit 208, which is preferably positioned within a transmitter, dongle, or removable cap. In some embodiments, the condition responsive element 206 is located in the heat cycle detection unit 208, rather than the measurement probe 202. In some embodiments, the heat cycle detection unit 208 is physically separable from the measurement probe 202. The heat cycle detection unit 208 includes a detection module 209, a data memory 211, and an interface 212. In one method of using the measurement device 200 of FIG. 2, the measurement probe 202 is disconnected from the heat cycle detection unit 208 and from any power source prior to being placed within an autoclave. Autoclaving is then initiated. The condition responsive element 206 deforms or otherwise changes shape in response to the temperature or pressure in the autoclave increasing to near or above a certain threshold. The set threshold for a given condition responsive element 206 is determined by the materials and configuration of the condition responsive element 206. The condition responsive element 206 may have a range of a few degrees within which it undergoes deformation. In some such embodiments, the condition responsive element 206 is a bimetallic strip or a shape memory alloy that deforms in response to an increase in temperature. In some embodiments, when the condition responsive element 206 deforms, it or another movable member in contact with the condition responsive element 206 mechanically locks into a second position, remaining in the second position even as the temperature drops. In one embodiment of the method, after the autoclaving is complete, the measurement probe 202 is removed from the autoclave and connected to the heat cycle detection unit 208. During or upon connection to the measurement probe 202, the heat cycle detection unit 208 detects the presence of an element locked in a second position. The heat cycle detection unit 208 resets the element, causing the element to move back to a first position, and the detection module 209 stores a sterilization or cleaning cycle (e.g. autoclave cycle) count in the data memory 211. Although in some embodiments the heat cycle detection unit comprises an atmospheric pressure responsive element, and thus the heat cycle detection unit is responding to atmospheric rather than temperature events, those of skill in the art will understand that the change in atmospheric pressure within the probe is associated with an autoclave cycle and also signals that a heat cycle has occurred.

Figure 3B:
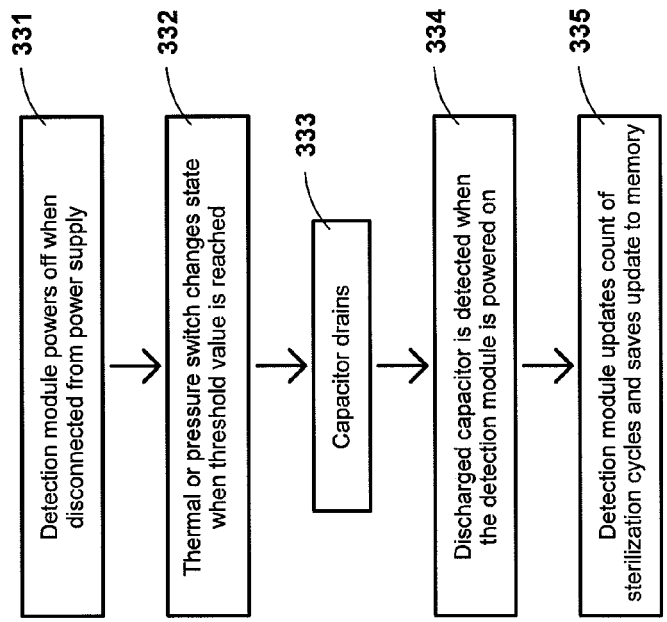
FIG. 3B is a flowchart illustrating one method of operations performed by the measurement device of FIG. 3A.
Figure 3A:
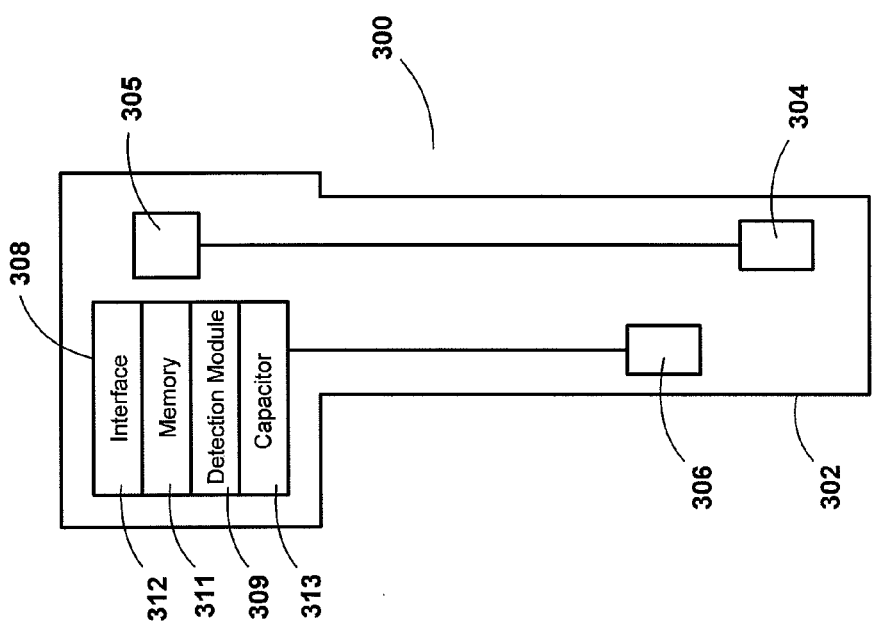
FIG. 3A depicts a block diagram of another embodiment of a measurement device.

FIG. 3A provides a schematic of another measurement device embodiment. In FIG. 3A, the measurement device 300 includes a measurement probe 302 having a sensor 304 and a condition responsive element 306. In some embodiments, the condition responsive element 306 is located in the heat cycle detection unit 308, rather than the measurement probe 302. The sensor 304 is electrically coupled to a measurement interface 305 configured to provide probe operators with information about the environmental condition being sensed by the measurement probe 302. The condition responsive element 306 is electrically connected to a heat cycle detection unit 308, which includes a detection module 309, a data memory 311, a capacitor 313, and an interface 312. In some embodiments, the interface 312 and interface 305 are the same interface.

A method of operations for the measurement device embodiment of FIG. 3A, is shown in the flowchart of FIG. 3B. When describing the functions of specific components, reference numbers from FIG. 3A will be used. At block 331, the measurement device 300 is disconnected from an external power supply, causing the detection module 309 to power down. The measurement device 300 can then be placed in an autoclave chamber and subjected to the high temperatures and pressures of an autoclave cycle. At block 332, the condition responsive element 306, which is in the form of a mechanical thermal switch or pressure switch, moves or deforms at a set threshold temperature or pressure value, respectively, with the set threshold value determined by the physical and chemical properties of the switch 306. The deformation/movement of the switch 306 closes an electrical contact within a circuit. As shown at block 333, the closing of the electrical contact within the circuit causes a capacitor or similar charge storage unit 313 to drain. In some embodiments, the switch 306 returns to a first, non-deformed position when the temperature or pressure falls below the threshold value, which returns the circuit to its first state. The capacitor remains drained until the measurement device 300 is reconnected to a power supply and additional current flows to the capacitor 313. As shown in block 334, after the measurement device 300 is reconnected to a power supply, the detection module 309 powers back on and detects the discharged capacitor 313. In response, as shown in block 335, the detection module 309 updates a count of heat cycle events and saves the updated count to the data memory 311.

Figure 4B:
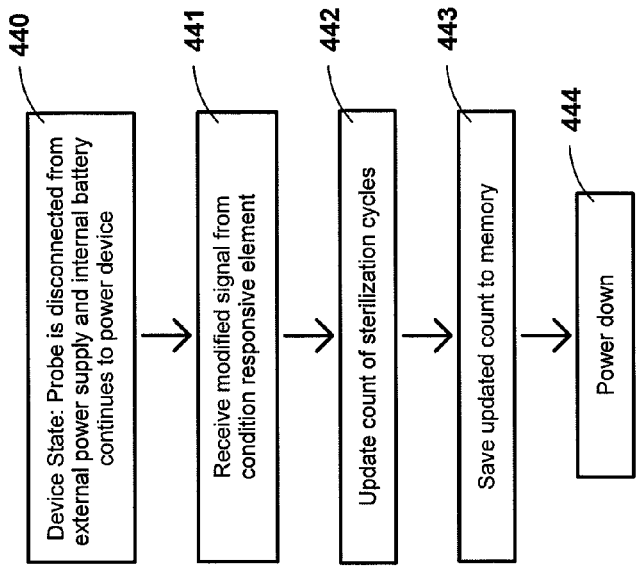
FIG. 4B is a flowchart illustrating one method of operations performed by the measurement device of FIG. 4A.
Figure 4A:
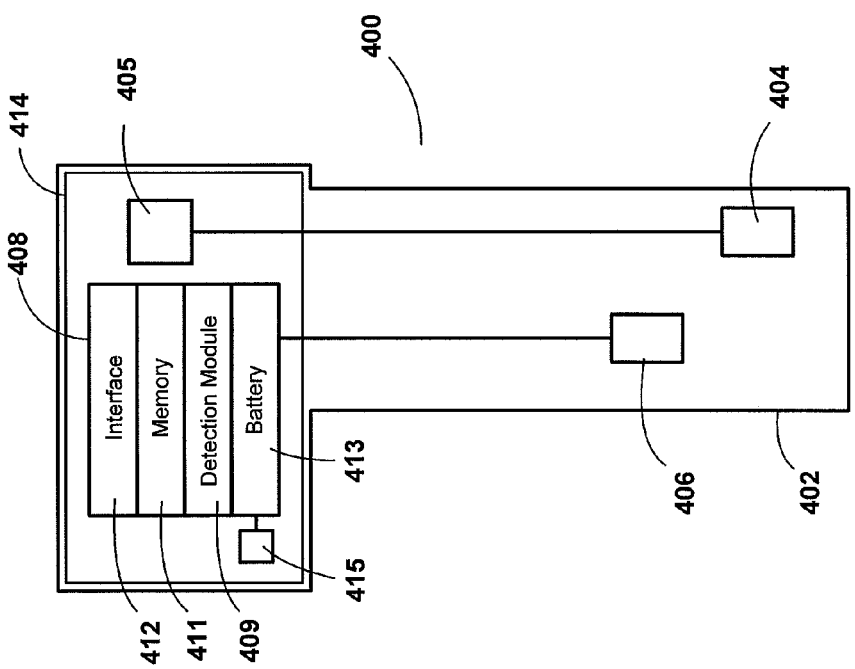
FIG. 4A depicts a block diagram of another embodiment of a measurement device.

An additional embodiment of a measurement device is depicted schematically in FIG. 4A. As in the previous embodiment, the measurement device 400 includes a measurement probe 402 having a sensor 404 electrically coupled to a measurement interface 405 and a condition responsive element 406 electrically coupled to a heat cycle detection unit 408. In some embodiments, the condition responsive element 406 is located in the heat cycle detection unit 408, rather than the measurement probe 402. The heat cycle detection unit 408 includes a detection module 409, a data memory 411, and an interface 412. In the present embodiment, the detection module 409 is preferably a microprocessor programmed to control the heat cycle detection unit 408 and programmed to transform analog signals received from the condition responsive element 406 to digital signals. The interface 412 is preferably a wireless transmitter configured to output wireless signals, such as, for example, near-field communication, Bluetooth, Wi-Fi, or radiofrequency signals. The interface 412 of some embodiments includes multiple wireless transmitters capable of outputting multiple forms of wireless signals. In some embodiments, the wireless signals are received by, and displayed on, a handheld device having a display screen. Additionally or alternatively, the interface 412 of some embodiments includes a data bus for wired digital outputs. In some embodiments, the interface 412 and interface 405 are the same interface.

In FIG. 4A, the capacitor 313 of FIG. 3A has been replaced with a battery 413. In other embodiments, the measurement device includes both a battery and a capacitor. In the depicted embodiment, the battery 413 is part of the heat cycle detection unit 408, disposed within a housing unit 414. In other embodiments, the battery 413 is electrically coupled to the detection module 409 but physically separable from the heat cycle detection unit 408. In some embodiments, the battery 413 is readily accessible to facilitate battery replacement. In some embodiments, the battery in FIG. 4A is a rechargeable battery. In other embodiments, a disposable battery is used. The battery 413 functions as a portable power source, thereby allowing at least some of the electronics within the measurement device 400 to remain powered when the device 400 is disconnected from an external power source. Consequently, the heat cycle detection unit 408 is configured to continue functioning when the measurement device 400 is placed within an autoclave chamber, or otherwise disconnected from an external power source, e.g. during a steam-in-place cycle. The embodiment of FIG. 4A additionally includes a power-gathering system 415. The power-gathering system 415 can include any portable element capable of converting energy from light into voltage or current, such as, for example, a photodiode or a photovoltaic cell. In the embodiment of FIG. 4A, a photodiode 415 is included to trickle charge the battery 413 to help maintain charge in the system.

FIG. 4B provides a flowchart depicting a method of counting exposures to sterilization or cleaning cycles performed by the detection module 409 of FIG. 4A. At block 440 the probe is disconnected from the external power supply and the internal battery continues to power the device. At block 441, the detection module 409, which is electrically coupled to the condition responsive element 406, receives a modified signal from the condition responsive element 406. In the embodiments of FIGS. 4A-4B, the condition responsive element 406 is an electrical resistive element, for example, a thermistor or RTD, which experiences significant changes in resistance with changing temperature. In other embodiments, the condition responsive element 406 is an atmospheric pressure sensor, which generates a changed signal, for example, due to a change in resistance or inductance, as the surrounding pressure changes. The detection module 409 of various embodiments is configured to detect changes in the received signal. The detection module 409 is also programmed to determine, using known equations, when the changed signal indicates that a select threshold temperature or pressure has been reached.

In other embodiments (not shown), the condition responsive element is a condition responsive circuit that includes a thermal or pressure switch. In some such embodiments, when the temperature or pressure rises near or above a threshold level, the thermal switch or pressure switch changes state, causing the condition responsive circuit to open. The detection module (which receives power from a battery to which it is connected via an alternate circuit), detects the cessation of current in the condition responsive circuit. In other such embodiments, when the temperature or pressure rises near or above a threshold level, a thermal switch or pressure switch changes state, causing a condition responsive circuit to close. The detection module (which receives power from a battery to which it is connected via an alternate circuit), detects the flow of current in the condition responsive circuit. Through such mechanisms, the detection module, in effect, detects that the threshold temperature or pressure value has been reached.

As shown at block 442 and 443, when the detection module 409 detects that the threshold temperature or pressure has been reached, the count of heat cycle events is updated and saved in the data memory 411. In some embodiments, the detection module 409 increments a counter and stores the new count within the data memory 411. In other embodiments, the detection module 409 stores the date, and optionally the time, of heat cycle (e.g. autoclave) detection in the data memory 411.

To protect the circuitry from extreme temperatures and pressures, the detection module 409 then optionally powers down, as shown at block 444 (if the circuitry of the device can operate under high temperature/pressure, the device need not power down). To better protect the circuitry, in some embodiments, a threshold temperature or pressure is selected that is lower than the ranges described above. For example, in biotechnology, measurement probes are often used to monitor processes occurring at a temperature range around 37 degrees Celsius, such as, for example, 35-40 degrees Celsius. In such industries, measurement devices may be selected having a threshold temperature of 60-70 degrees Celsius, for example. It will be appreciated by those having ordinary skill in the art that any threshold temperature or pressure may be selected for counting sterilization or cleaning cycles that is above the maximum temperature or pressure experienced by the measurement device during normal (non-sterilization or cleaning) operations.

An additional embodiment of a measurement device is depicted schematically in FIG. 5A. As in the previous embodiment 4A, the measurement device 500 includes a measurement probe 502 having a sensor 504 electrically coupled to a measurement interface 505 and a condition responsive element 506 electrically coupled to a heat cycle detection unit 508. In some embodiments, the condition responsive element 506 is located in the heat cycle detection unit 508, rather than the measurement probe 502. The heat cycle detection unit 508 includes a detection module 509, a data memory 511, and an interface 512. In the present embodiment, the detection module 509 is preferably a microprocessor programmed to control the heat cycle detection unit 508. The interface 512 is preferably a wireless transmitter configured to output wireless signals, such as, for example, near-field communication, Bluetooth, Wi-Fi, or radiofrequency signals. The interface 512 of some embodiments includes multiple wireless transmitters capable of outputting multiple forms of wireless signals. In some embodiments, the wireless signals are received by, and displayed on, a handheld device having a display screen (not shown). Additionally or alternatively, the interface 512 of some embodiments includes a data bus for wired digital outputs. In some embodiments, the interface 512 and interface 505 are the same interface.

In FIG. 5A, the capacitor 313 of FIG. 3A has been replaced with a battery 513 and a capacitor or similar charge storage element 514. In the depicted embodiment, the battery 513 is part of the heat cycle detection unit 508, disposed within a housing unit 515. In other embodiments, the battery 513 is electrically coupled to the detection module 509 but physically separable from the heat cycle detection unit 508. In some embodiments, the battery in 513 is readily accessible to facilitate battery replacement. In some embodiments the battery in FIG. 5A is a rechargeable battery. In other embodiments, a disposable battery is used. The battery 513 functions as a portable power source, thereby allowing at least some of the electronics within the measurement device 500 to power up on its own when the device 500 is disconnected from an external power source. Consequently, the heat cycle detection unit 508 is configured to power on when the measurement device 500 is placed within an autoclave chamber (or otherwise disconnected from and external power source) and the condition responsive element 506 changes state when it exceeds its threshold limit.

FIG. 5B provides a flowchart depicting a method of counting exposures to sterilization or cleaning cycles performed by the detection module 509 of FIG. 5A. At block 550 the device has been disconnected from an external power source whereupon the device automatically powers down. At block 551, the condition responsive element 506, in this embodiment a thermal switch, changes state in response to the temperature rising above the threshold value. This change in state closes the thermal switch which in turn supplies internal battery power 513 to the detection module 509 and the memory 511 and begins charging capacitor 514. At block 552 the detection module 509 increments the heat cycle counter, and saves the new number in memory 511. In block 553 the capacitor has now completely charged and this causes power to be shut off to the detection module and memory which in turn saves battery power and protects the microprocessor in 509 and other components of the detection unit 508 from operating in the excessive heat of an autoclave cycle. In block 554, heat event ends, the probe's temperature sinks back down past the threshold value of the thermal switch 506, the switch changes back to its original open state, the battery is disconnected from the circuit, and the capacitor discharges. As a result of the automatic actions in block 554 the device is now in a state represented by block 555 where the device is now off, conserving the battery 513, and ready to automatically and autonomously auto-start again when the next heat cycle begins.

FIG. 6A provides a schematic of another embodiment of a measurement device 600 having a battery 613 and a heat cycle detection unit 608. The heat cycle detection unit 608 includes a detection module 609, a data memory 611, and an interface 612. As in previous embodiments, the measurement device 600 also includes a measurement probe 602 with a sensor 604 electrically coupled to a measurement interface 605. In other embodiments, the sensor 604 is electrically coupled to the detection module 609. In such embodiments, the detection module 609 is configured to amplify the signal received from the sensor 604 and convert it to a digital output. The digital output can then be provided to an output device via the interface 612 in a similar manner as the sterilization or cleaning count data that is transmitted to an output device via the interface 612. In addition, in some embodiments a capacitor or other charge storage unit (not shown) is included and functions as described in FIG. 5.

The measurement device 600 of FIG. 6A also has a vessel coupling device 618, which is configured to secure the measurement device 600 to a perimeter wall or lid (i.e., the body) of a processing vessel. In various embodiments, the measurement device 600 is secured to the body of a processing vessel such that a distal portion 620 of the measurement device 600 is disposed within an interior cavity of the vessel and a proximal portion 622 of the measurement device 600 is positioned outside the vessel.

In some embodiments, the measurement device includes only one condition responsive element. In such embodiments, if the condition responsive element is positioned on or within a proximal portion of the measurement device, it will not be subjected to, nor respond to, temperature or pressure changes that occur within the processing vessel. Consequently, if a steam-in-place cycle or clean-in-place cycle is run within the processing vessel, the condition responsive element will not respond, and the sterilization or cleaning cycle will not be counted. In contrast, autoclaving requires placement of the entire measurement probe within an autoclave chamber. Consequently, even condition responsive elements positioned on or within a proximal portion of the measurement device will experience the elevated temperatures and pressures of an autoclave cycle. Thus, when a condition responsive element is only positioned within a proximal portion of the measurement device, the measurement device is tailored to count, specifically, autoclave cycles.

Conversely, if only one condition responsive element is present and positioned on or within a distal portion of the measurement device, the condition responsive device will be subjected to any elevated temperatures and pressures that occur within the processing vessel as well as elevated temperatures and pressures that occur while the measurement device is disposed within an autoclave chamber. In such embodiments, the measurement device is configured to detect and count multiple forms of sterilization or cleaning cycles. Each detected cycle is counted and stored in memory as a generic sterilization or cleaning cycle.

In some measurement device embodiments, such as the embodiment of FIG. 6A, the measurement device 600 includes both a condition responsive element 606 positioned on or within the distal portion 620 and a condition responsive element 607 positioned on or within the proximal portion 622. Such embodiments may be configured to detect and count multiple forms of heat cycles and distinguish between the various forms.

A method of detecting, distinguishing, and counting various forms of sterilization or cleaning is provided in the flowchart of FIG. 6B. As shown in block 660, the detection module 609 receives a modified signal from a condition responsive element 606 or 607 as the temperature or pressure rises. From the modifications in the signal, the detection module 609 determines when a threshold temperature or pressure has been reached, as shown in block 661. In block 662, the detection module 609 determines whether the modified signal is being received from the proximal condition responsive element 607. If it is, then the entire measurement device 600 is being subjected to an elevated temperature and/or pressure, and one can conclude that the measurement device 600 is in an autoclave chamber undergoing an autoclave cycle. In such cases, the detection module 609 is programmed to update a count of autoclave cycles (and/or a count of generic sterilization or cleaning cycles) as indicated in block 666, save the updated count in the data memory 611 as indicated in block 667, and optionally power down the detection module 609 to protect the electronics in the heat cycle detection unit 608, as indicated in block 668.

If the detection module 609 determines that the modified signal is not being received from the proximal condition responsive element 607, (and thus, is instead coming from only the distal condition responsive element 606), the detection module 609 is programmed to update a count of steam-in-place cycles (and/or a count of generic sterilization or cleaning cycles) as indicated in block 663, and save the updated count in the data memory 611 as indicated in block 664. The detection module 609 may optionally be programmed to power down in response to detecting the heat cycle, although such programming is not necessary for steam-in-place cycles when the heat cycle detection unit electronics are located outside the processing vessel.

Figure 7B:
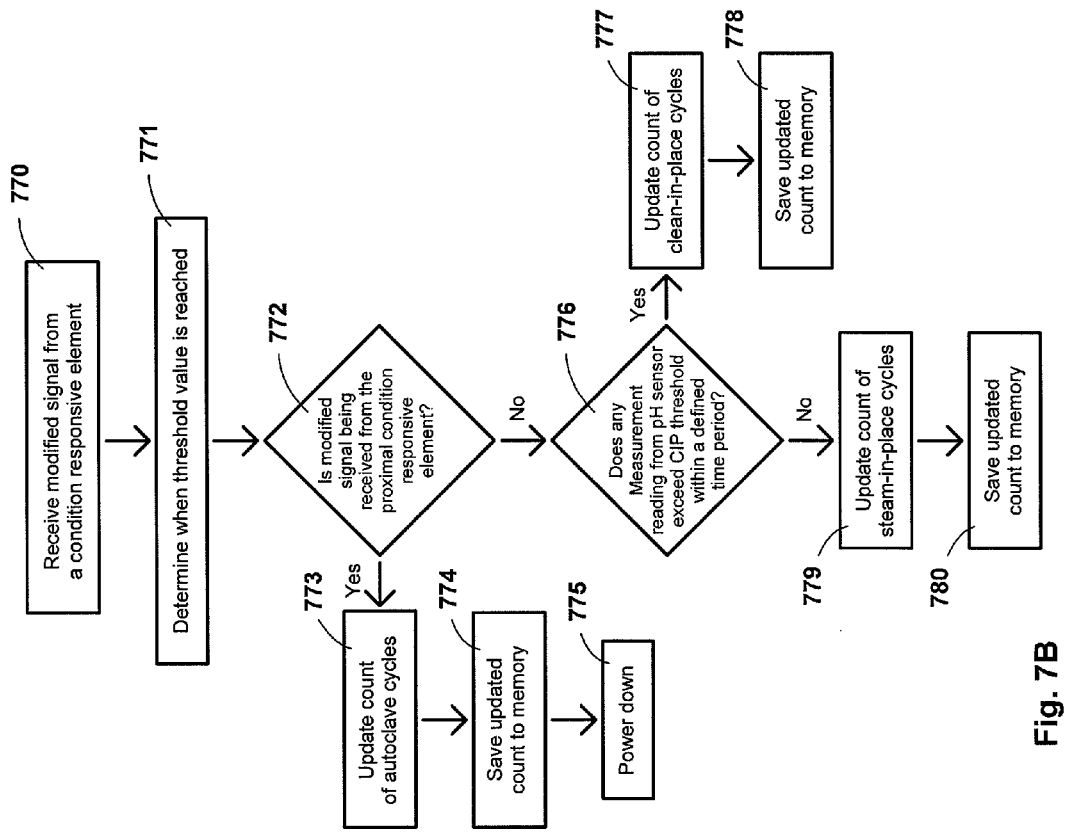
FIG. 7B is a flowchart illustrating one method of operations performed by the measurement device of FIG. 6A.
Figure 7A:
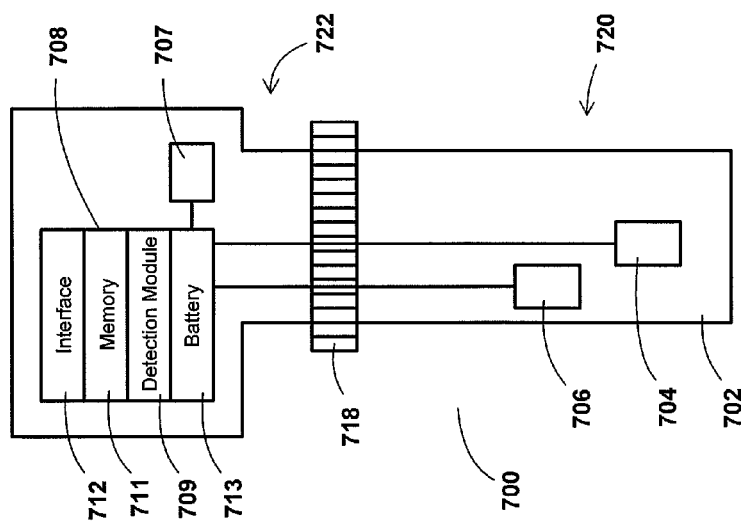
FIG. 7A depicts a block diagram of another embodiment of a measurement device.

FIG. 7A schematically depicts an embodiment of a measurement device 700 configured to detect clean-in-place cycles, along with, preferably, autoclave cycles. The provided measurement device 700 includes a heat cycle detection unit 708 having an interface 712, a data memory 711, a detection module 709, and a battery 713. The measurement device 700 also includes a measurement probe 702 having a pH sensor 704 disposed on or within the probe 702. The pH sensor 704 of the current embodiment is electrically coupled to the heat cycle detection unit 708. In some embodiments, the pH sensor 704 is provided to help detect clean-in-place cycles, and the measurement probe 702 includes one or more other sensors configured to sense a condition of the processing medium. In other embodiments, the pH sensor 704 serves as both the primary sensor of the measurement probe 702 and the sensor used during detection of clean-in-place cycles, and thus may be coupled to an interface (not shown) which is used during normal operation for monitoring pH levels.

In FIG. 7A, a vessel coupling device 718 is permanently or separably affixed to an outer portion of the measurement probe 702. A first temperature responsive element 706 is positioned on or within a distal portion 720 of the measurement device 700, and a second condition responsive element 707 is positioned on or within a proximal portion 722 of the measurement device 700.

FIG. 7B depicts one embodiment of a method performed by the measurement device of FIG. 7A when counting clean-in-place and other heat cycle events. The detection module 709 receives signals from the condition responsive elements 706 and 707, and the signals change as the temperature or pressure increases and/or crosses a threshold. As shown in blocks 770 and 771, detection module 709 receives a modified signal from a condition responsive unit, and from the signal, determines when a threshold value has been reached. The detection module 709 also performs the operation in block 772 to determine if the modified signal was received from the proximal condition responsive element 707. If it was, then the detection module 709 follows the autoclave detection protocol described previously. As shown in blocks 773-775, the detection module 709 updates a count of autoclave cycles, saves the updated count to the data memory 711, and optionally powers down (if the circuitry of the device can operate under high temperature/pressure, the device need not power down). If the modified signal was not received from the proximal condition responsive element 707, (and thus, is instead coming from only the distal condition responsive element 706), the detection module 709 processes signal inputs from the pH sensor 704. In block 776, the device determines if any measurement reading from the pH sensor 704 exceeds a clean-in-place pH threshold within a defined time period, a clean-in-place detection protocol is performed (blocks 777-778). If no pH reading exceeds the clean-in-place threshold during the defined time period, the steam-in-place detection protocol is performed (block 779-780). The clean-in-place protocol, shown in blocks 777 and 778, involves updating a count of clean-in-place cycles and saving the updated count to the data memory 711. Similarly, the steam-in-place protocol, shown in blocks 779 and 780, includes updating a count of steam-in-place cycles and saving the updated count to the data memory 711. The detection module 709 can further be optionally programmed to shut down in response to detection of a steam-in-place cycle and/or a clean-in-place cycle.

In some embodiments, the clean-in-place threshold is at least 60 degrees Celsius and less than 100 degrees Celsius. Typically, the clean-in-place threshold is between 65 and 90 degrees Celsius, and it can include any sub-range or individual value within that disclosed range, including 65, 70, 75, 80, 85 and 90 degrees Celsius. In some embodiments, the pH threshold is within the ranges of either 9 to 14 pH or 1 to 4 pH and may be any sub-range or individual value therebetween. For example, the clean-in-place pH threshold of some embodiments is 9, 10, 11, 12, 13, or 14. In some embodiments, the defined period of time is between about 30 seconds and about 5 minutes, and includes any sub-range or individual value therebetween, including 0.5-4, 0.5-3, 0.5-2, 1-5, 1-4, 1-3, 1-2, 2-5, 2-4, and 2-3 minutes. The defined period of time includes both the about 30 seconds to about 5 minutes preceding the temperature-threshold-reaching event and the about 30 seconds to about 5 minutes following the temperature-threshold-reaching event.

In some embodiments of a measurement device, the measurement device can both automatically power up (i.e., auto-start) and automatically power itself off at certain points in a heat sterilization or cleaning, or autoclave cycle. This auto-start feature may advantageously provide for more accurate counting of heat cycles as well as provide better power management of the battery and thus longer shelf life of the probe. For example, without an auto-start feature, if multiple successive heat cycles are performed on a measurement device without turning it on between cycles, only one cycle will be counted. In some embodiments, that cycle is counted during the cycle, just prior to the measurement device shutting down. In other embodiments, a cycle is counted when the measurement device powers back on, for example, by detecting a drained capacitor. By either method it is desirable to have the probe automatically self-start whenever a heat cycle begins again. By automatically powering back on as a cycle starts, the measurement device of the current embodiment is ready to detect and count each new cycle that occurs. By use of a thermal switch as a condition responsive element the device can be configured to auto-start each time there is a new heat cycle. Furthermore, since the device can auto-start at the beginning of the heat cycle, there is no need to keep it on after the counter is incremented and the device can shut itself off for the remainder of the cycle to conserve the battery and protect the microprocessor from excessive heat.

Figure 8:
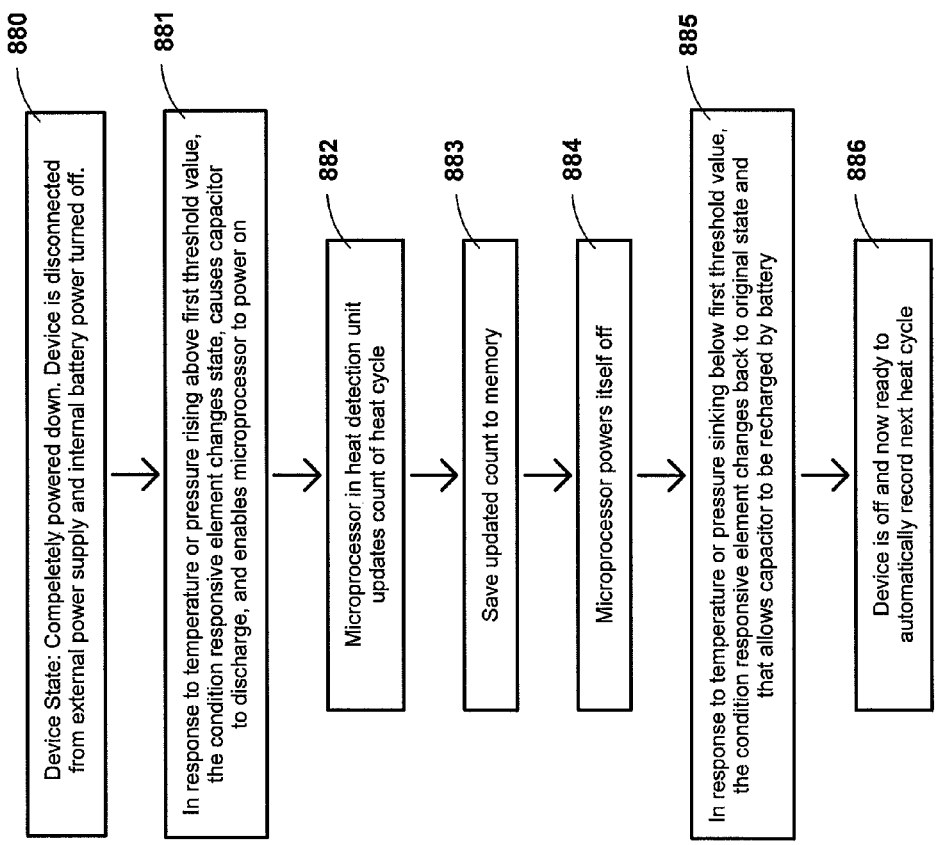
FIG. 8 depicts a block diagram of another embodiment of a measurement device.

Measurement device embodiments that perform the method of FIG. 8 include an integral power supply, such as a battery. In some embodiments, both a battery and a capacitor are included. In some embodiments the power, supply is augmented by a portable power supply such as an attachable battery. In block 880 the device is in a state of complete power down. The device is disconnected from the external power supply and the internal battery power is turned off. In block 881 the condition responsive element changes state at a predetermined temperature threshold, discharges a capacitor, and switches power on to the device. In block 882 the detection module detects that the capacitor has been discharged and this signals that a heat cycle has begun. In block 883 the count is incremented by 1 in memory and saved. In block 884 the device powers off the microprocessor for it to better endure the extreme temperatures of an autoclave cycle and to conserve the internal battery. In block 885 the probe's temperature cools to below the temperature threshold of the condition responsive device, the element's state changes back and the device's capacitor is recharged from the battery. In block 886 the device is once again completely powered down and ready to automatically count the next heat cycle.

Figure 9:
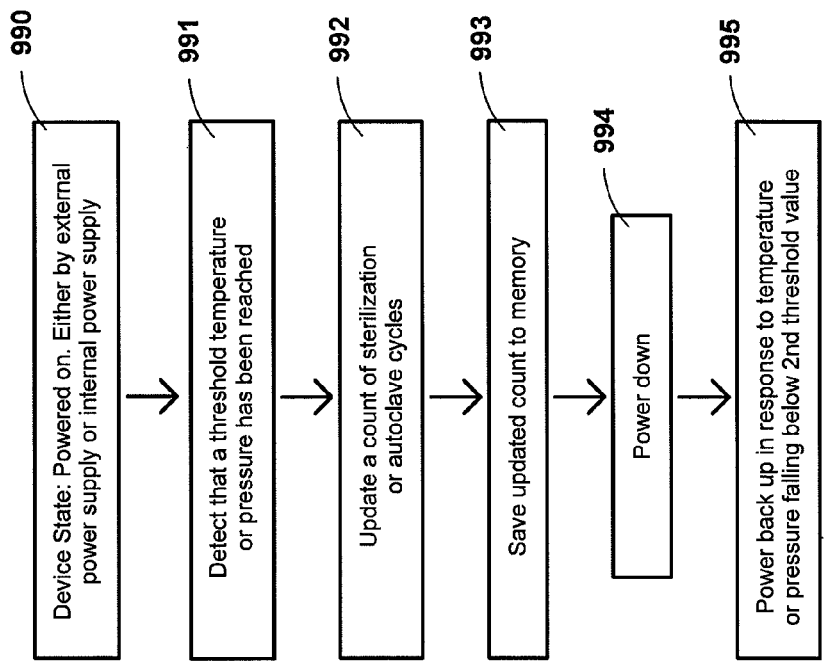
FIG. 9 depicts a block diagram of another embodiment of a measurement device.

Another method performed by some embodiments of a measurement device is provided in the flowchart of FIG. 9. In the depicted method, the measurement device can both automatically shut itself off and automatically turn itself back on (i.e., auto-start) at certain points in a heat sterilization or cleaning, e.g., autoclave cycle.

Measurement device embodiments that perform the method of FIG. 9 include a portable power supply, such as a battery. In some embodiments, both a battery and a capacitor are included. In block 990 at least the heat cycle detection portion of the device is powered on. As shown in blocks 991-994, the detection module of such measurement devices detects that a threshold temperature or pressure has been reached, updates a count of heat cycle event (e.g. autoclave), saves the updated count in the data memory, and optionally powers down (if the circuitry of the device can operate under high temperature/pressure, the device need not power down). In one embodiment, a thermal or pressure switch is used. When a threshold temperature or pressure is reached, the switch physically deforms and opens a circuit connecting the switch, capacitor, battery, and detection module. When this occurs, the battery no longer provides voltage and current to the detection module, and the capacitor or other charge storage unit begins to drain. The detection module receives current from the draining capacitor long enough to detect the opened switch and record the occurrence of a heat cycle event (sterilization or cleaning) in the data memory. The detection module powers down as the current wanes. As shown in block 995, when the temperature or pressure falls below a second threshold value (also referred to as a power-on temperature or pressure), the switch returns to its first, non-deformed position, which completes the circuit. Charge and voltage from the battery are again delivered to the detection module, and the detection module turns back on. In embodiments having one universal switch that functions to both power off and power on the detection module, the first threshold value and second threshold value are generally equal. Shape memory materials and bimetallic strips are generally configured to deform and reform to their original shapes at substantially similar or equal temperatures.

In an alternative embodiment, the detection module may perform blocks 991-994 in response to receiving a changing signal from an electrical condition responsive element. From the change in signal, the detection module is configured to calculate/detect that a first threshold value has been reached. In such an embodiment, a second condition responsive element in the form of a mechanical switch is included in a second circuit in the measurement device. The detection module is configured to automatically power up, as recited in block 995, when the mechanical switch changes state and closes an electrical contact in the second circuit. This occurs when a second threshold value is reached. In such embodiments, the first threshold value may be the same or different than the second threshold value. In some embodiments, the counter increments after the heat cycle ends, rather than at the start of the heat cycle.

Figure 10:
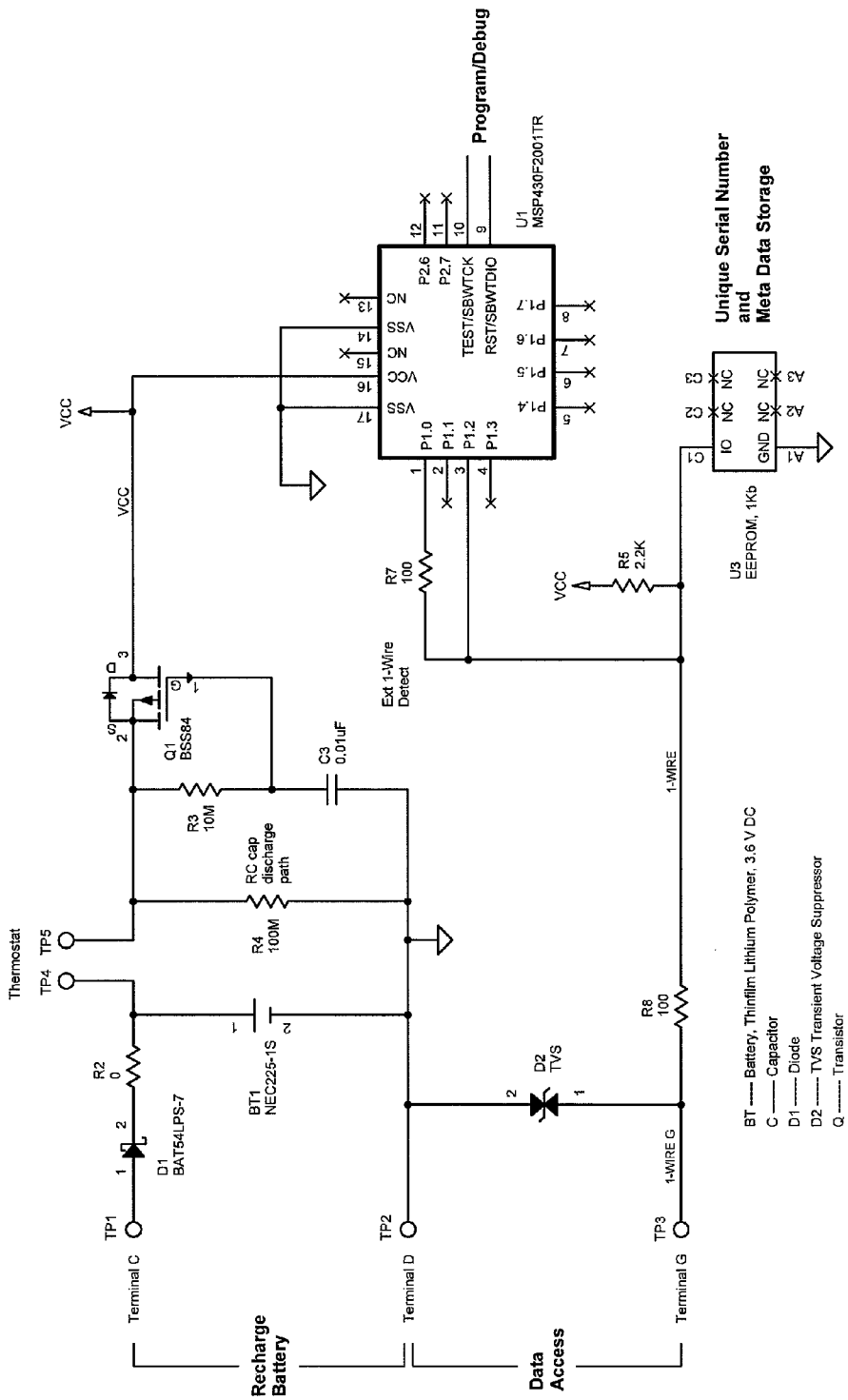
FIG. 10 depicts a circuit diagram for an embodiment of a heat cycle detection unit.
Figure 11:
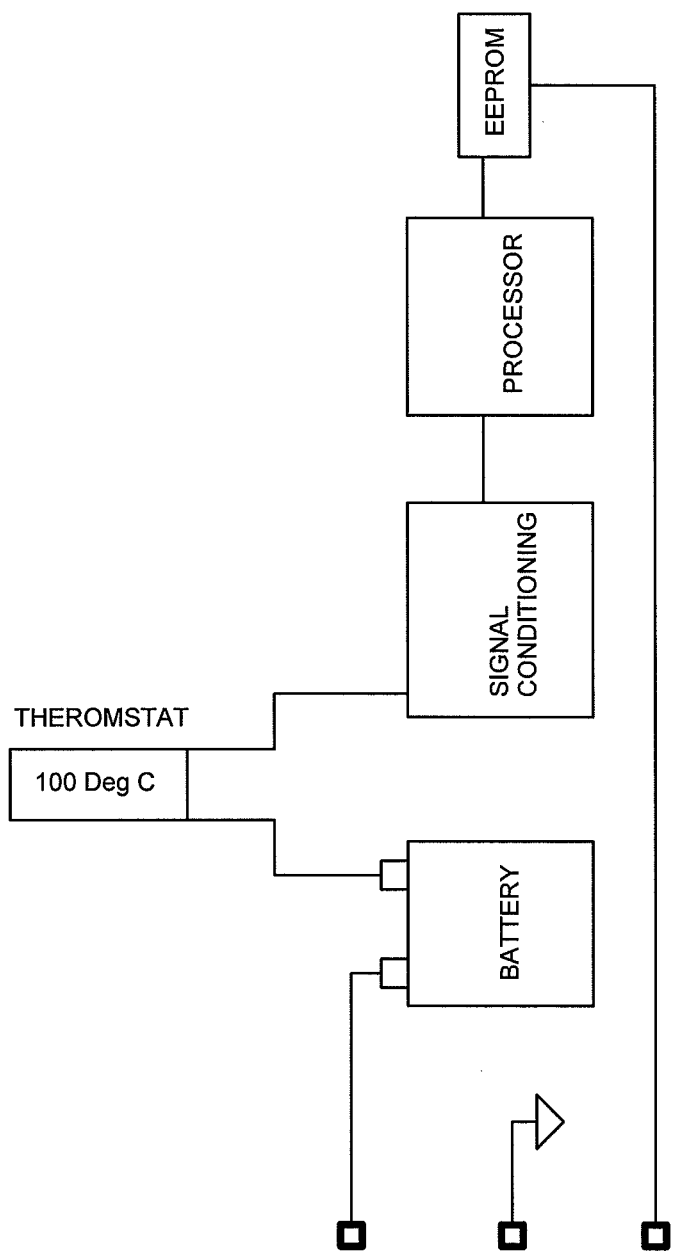
FIG. 11 depicts a schematic circuit diagram for an embodiment of a heat cycle detection unit.

FIG. 10 depicts a circuit diagram of one embodiment of a heat cycle detection unit. This particular embodiment automatically detects and records heat cycles according to the embodiment described with reference to FIG. 5B. FIG. 11 is a schematic of a circuit diagram of one embodiment of a heat cycle detection unit The various operations and methods described above may be performed by any suitable means capable of performing the operations, such as various hardware and/or software component(s), circuits, and/or module(s). Generally, any operations illustrated in the Figures may be performed by corresponding functional means capable of performing the operations.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the embodiments of the invention.

For purposes of summarizing the disclosure, certain aspects, advantages and features have been described herein. It is to be understood that not necessarily all such advantages may be achieved in accordance with any particular embodiment. Thus, the invention may be embodied or carried out in a manner that achieves or optimizes one advantage or group of advantages as taught herein without necessarily achieving other advantages as may be taught or suggested herein.

While this invention has been described in connection with what is are presently considered to be practical embodiments, it will be appreciated by those skilled in the art that various modifications and changes may be made without departing from the scope of the present disclosure. It will also be appreciated by those of skill in the art that parts mixed with one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. Thus, while the present disclosure has described certain exemplary embodiments, it is to be understood that the invention is not limited to the disclosed embodiments, but, on the contrary, is intended to cover various modifications and equivalent arrangements included within the scope of the appended claims, and equivalents thereof.

What is claimed is:

1. A measurement device adapted to withstand and automatically count a heat sterilization or cleaning cycle, comprising:
    a measurement probe comprising a sensor configured to detect a characteristic of a medium and generate a measurement signal;
    a condition responsive element comprising either a temperature responsive element or a pressure responsive element, wherein the condition responsive element is a first switch configured to transition from a first state to a second state when the first switch exceeds a first temperature or a first pressure; and
    a heat cycle detection unit comprising a detection module, a data interface, and a data memory; wherein the detection module is configured to:
        detect a heat cycle event using the condition responsive element, and
        record detection of the heat cycle event in the data memory in response to the first switch transitioning from the first state to the second state.

2. The measurement device of claim 1, wherein the heat cycle event is an autoclave cycle, a steam-in-place sterilization cycle, or a clean-in-place sanitizing cycle.

3. The measurement device of claim 1, wherein the device is configured to automatically power off the heat cycle detection unit after detection of the heat cycle event.

4. The measurement device of claim 1, wherein the device is configured to automatically power on the heat cycle detection unit at the beginning of the heat cycle event in response to a change of state of the condition responsive element.

5. The measurement device of claim 1, wherein the measurement probe and the heat cycle detection unit are fixedly integrated.

6. The measurement device of claim 1, further comprising a capacitor coupled to the first switch and configured to discharge in response to the first switch transitioning from the first state to the second state, wherein the detection module is configured to detect a discharged capacitor and record detection of a heat cycle event in the data memory.

7. The measurement device of claim 1, wherein the first switch is selected from a group consisting of: a bimetallic strip, an integrated thermal switch, and a pressure switch.

8. The measurement device of claim 1, wherein the heat cycle detection unit is configured to power on in response to the condition responsive element reaching a first temperature or a first pressure threshold.

9. The measurement device of claim 1, further comprising a coupling element configured to engage with a vessel body, wherein the measurement device includes a distal portion that is positioned within a vessel cavity and a proximal portion that is positioned external to the vessel cavity when the coupling element is engaged with the vessel body.

10. The measurement device of claim 1, wherein the sensor is selected from a group consisting of an amperometric, a potentiometric, an optical, a capacitive, and a conductive sensor.

11. The measurement device of claim 1, wherein the sensor is selected from a group consisting of a pH sensor, a temperature sensor, a dissolved oxygen sensor, and a combination thereof.

12. The measurement device of claim 1, wherein the detection module is selected from a group consisting of a circuit, a microprocessor, a Digital Signal Processor, an Application Specific Integrated Circuit, and a Field Programmable Gate Array.

13. The measurement device of claim 1, wherein the data interface is selected from a group consisting of a wireless transmitter, an input/output terminal, a data bus, and an industry standard 8 pin connector.

14. A method of automatically counting a heat cycle experienced by a measurement device, comprising:
    providing a measurement device comprising:
        a measurement probe having a sensor configured to detect a characteristic of a medium and generate a measurement signal, a condition responsive element comprising a first switch that transitions from a first state to a second state when the first switch exceeds a first temperature or a first pressure, and a heat cycle detection unit having a detection module, a data interface, and a data memory;

detecting a heat cycle event, using the condition responsive element; and recording detection of the heat cycle event in the data memory in response to the first switch transitioning from the first state to the second state.

15. The method of claim 14, wherein the heat cycle event is an autoclave cycle, a steam-in-place sterilization cycle, or a clean-in-place sanitizing cycle.

16. The method of claim 14, wherein the device is configured to automatically power off the heat cycle detection unit after detection of the heat cycle event.

17. The method of claim 14, wherein the device is configured to automatically power on the heat cycle detection unit at the beginning of the heat cycle event in response to a change of state of the condition responsive element.

18. The method of claim 14, further comprising discharging a capacitor coupled to the first switch in response to the first switch transitioning from the first state to the second state, wherein detecting a heat cycle event using the condition responsive element comprises detecting a discharged capacitor.

19. The method of claim 14, wherein the detection module records detection of a heat cycle event in the data memory in response to the condition responsive element exceeding a first temperature or a first pressure.

20. The method of claim 19, wherein the heat cycle detection unit powers on in response to the condition responsive element exceeding the first temperature or the first pressure.

* * * * *